United States Patent [19]
Hinchliffe

[11] Patent Number: 5,957,888
[45] Date of Patent: Sep. 28, 1999

[54] SURGICAL CANNULA HAVING A VARIABLE LENGTH

[75] Inventor: Peter W. J. Hinchliffe, New Haven, Conn.

[73] Assignee: United States Surgical Corporation, Norwalk, Conn.

[21] Appl. No.: 08/541,354

[22] Filed: Oct. 10, 1995

[51] Int. Cl.$^6$ .................................................. A61M 37/00
[52] U.S. Cl. ........................... 604/117; 604/164; 606/174
[58] Field of Search ................................ 604/117, 174, 604/96, 164, 165, 167, 169

[56] References Cited

U.S. PATENT DOCUMENTS

| | | |
|---|---|---|
| 3,039,468 | 6/1962 | Price . |
| 3,817,251 | 6/1974 | Hasson . |
| 4,022,191 | 5/1977 | Jamshidi .............................. 604/117 X |
| 4,670,008 | 6/1987 | Von Albertini .......................... 604/165 |
| 4,763,667 | 8/1988 | Manzo . |
| 4,911,694 | 3/1990 | Dolan . |
| 4,944,728 | 7/1990 | Carrell et al. . |
| 5,002,557 | 3/1991 | Hasson . |
| 5,122,122 | 6/1992 | Allgood . |
| 5,147,316 | 9/1992 | Castillenti . |
| 5,176,648 | 1/1993 | Holmes et al. . |
| 5,176,697 | 1/1993 | Hasson et al. . |
| 5,217,451 | 6/1993 | Freitas . |
| 5,232,451 | 8/1993 | Freitas et al. . |
| 5,290,249 | 3/1994 | Foster et al. ......................... 604/167 X |
| 5,308,325 | 5/1994 | Quinn et al. . |
| 5,330,497 | 7/1994 | Freitas et al. . |
| 5,336,176 | 8/1994 | Yoon . |
| 5,342,321 | 8/1994 | Potter . |
| 5,364,372 | 11/1994 | Danks et al. ......................... 604/164 X |
| 5,368,046 | 11/1994 | Scarfone et al. ..................... 604/117 X |
| 5,380,292 | 1/1995 | Wilson .................................... 604/164 |
| 5,383,860 | 1/1995 | Lau . |

FOREIGN PATENT DOCUMENTS

| | | |
|---|---|---|
| 0480653 | 4/1992 | European Pat. Off. . |
| 0589452 | 3/1994 | European Pat. Off. . |

*Primary Examiner*—Max Hindenburg

[57] ABSTRACT

A cannula assembly for insertion through tissue is provided having a housing and a cannula having a proximal end portion and a distal end portion. The cannula is supported at the proximal end portion by the housing. The cannula has a first predetermined length and is shortenable to a second predetermined length relative to the housing.

26 Claims, 11 Drawing Sheets

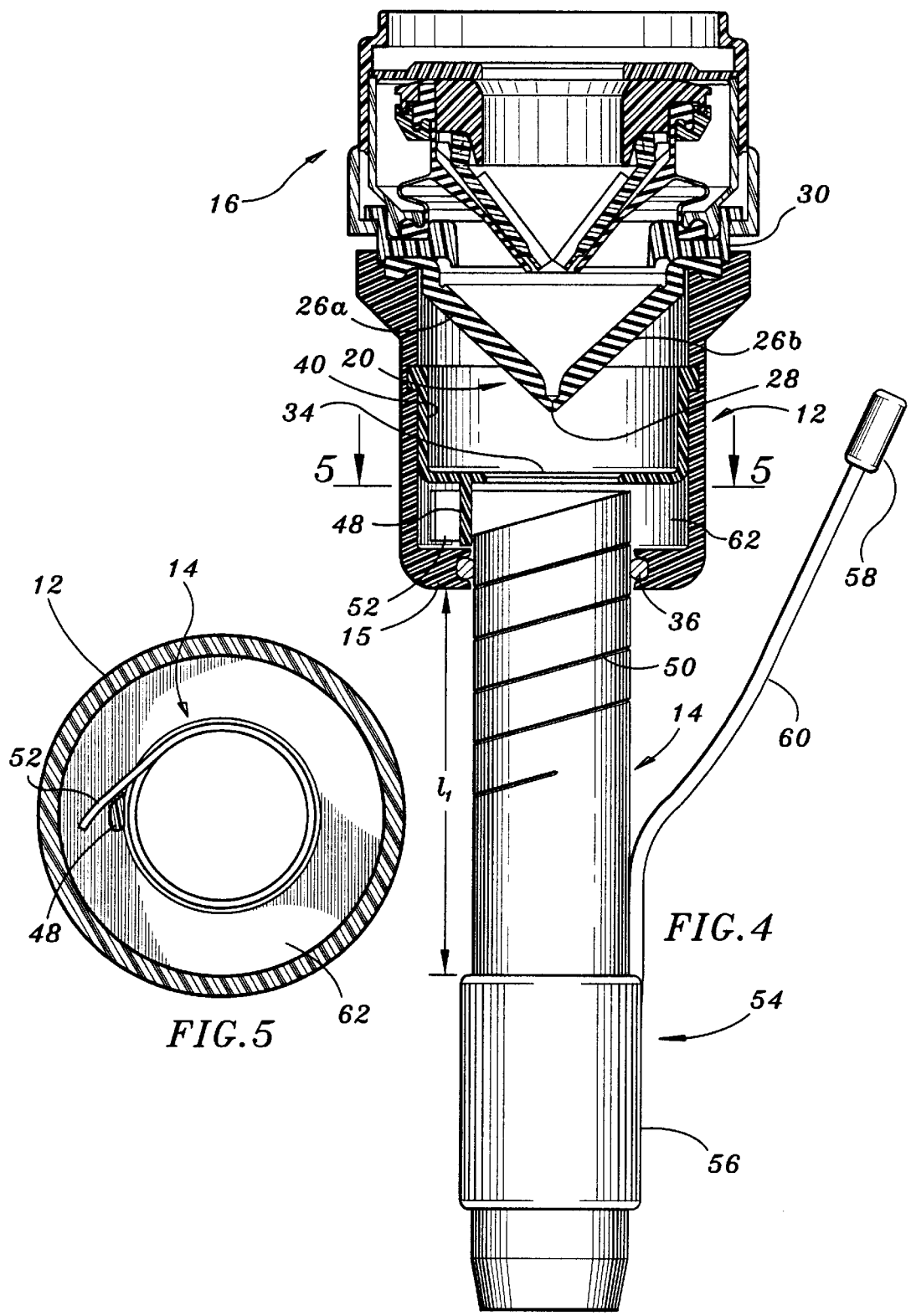

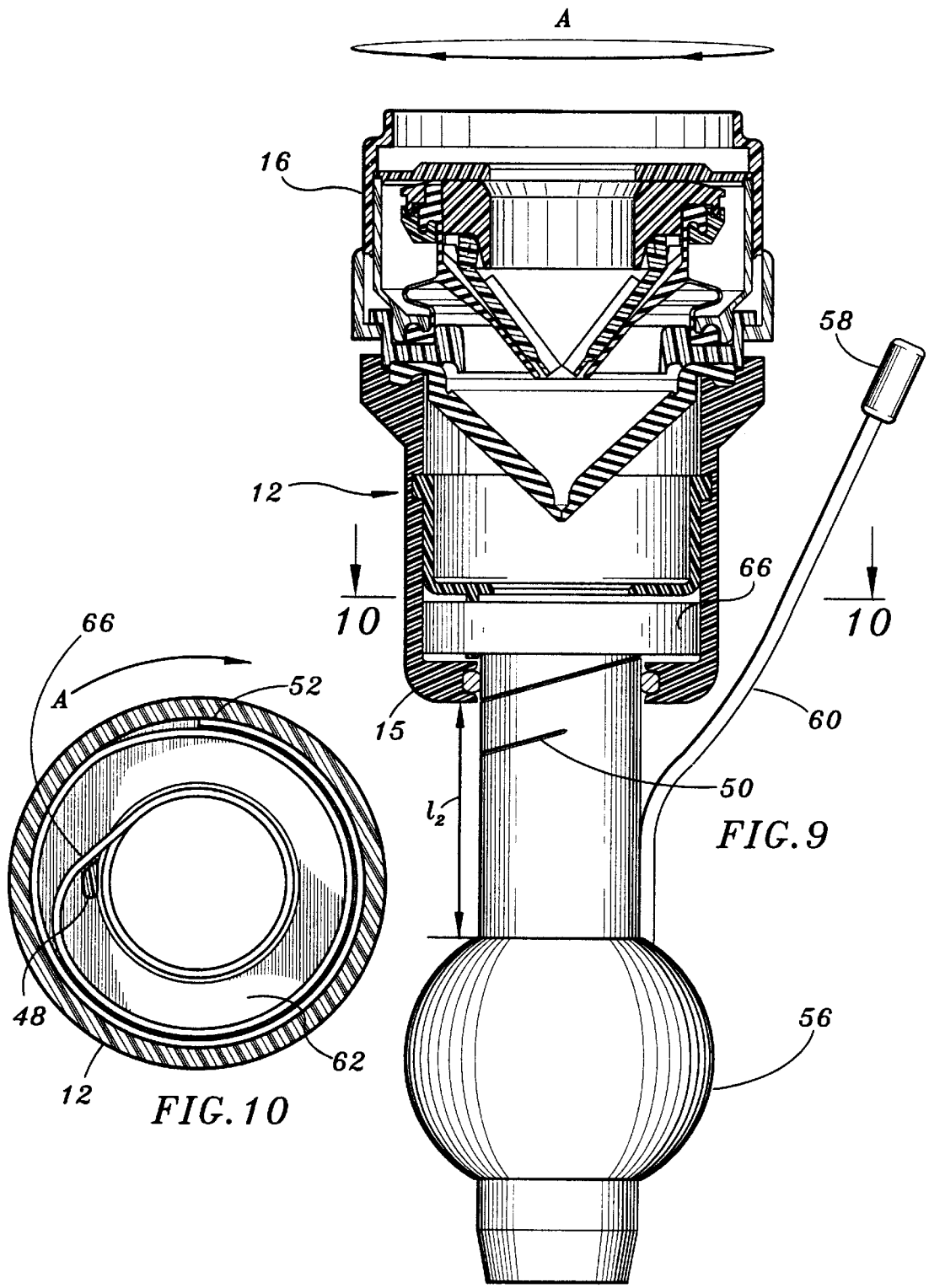

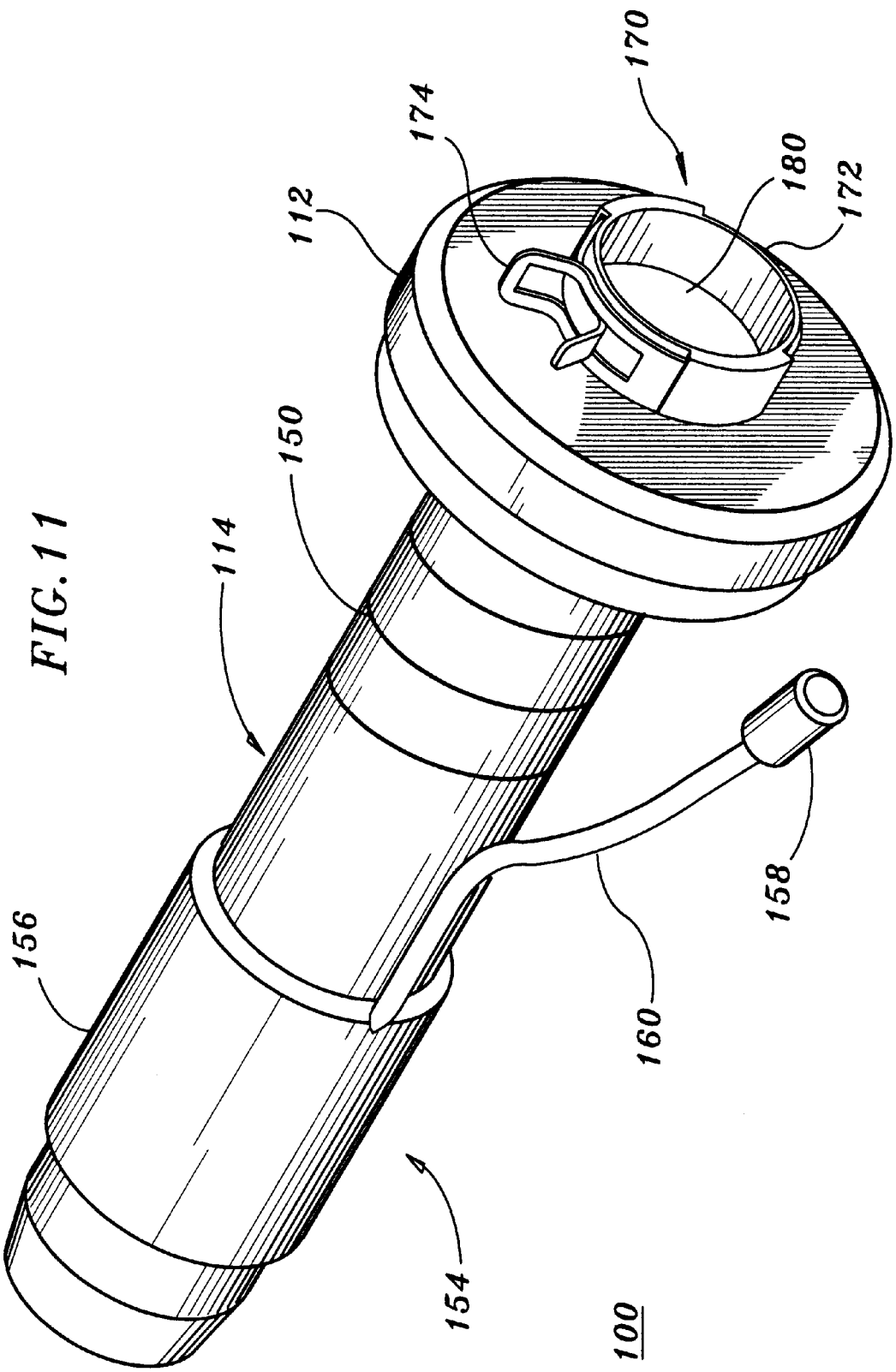

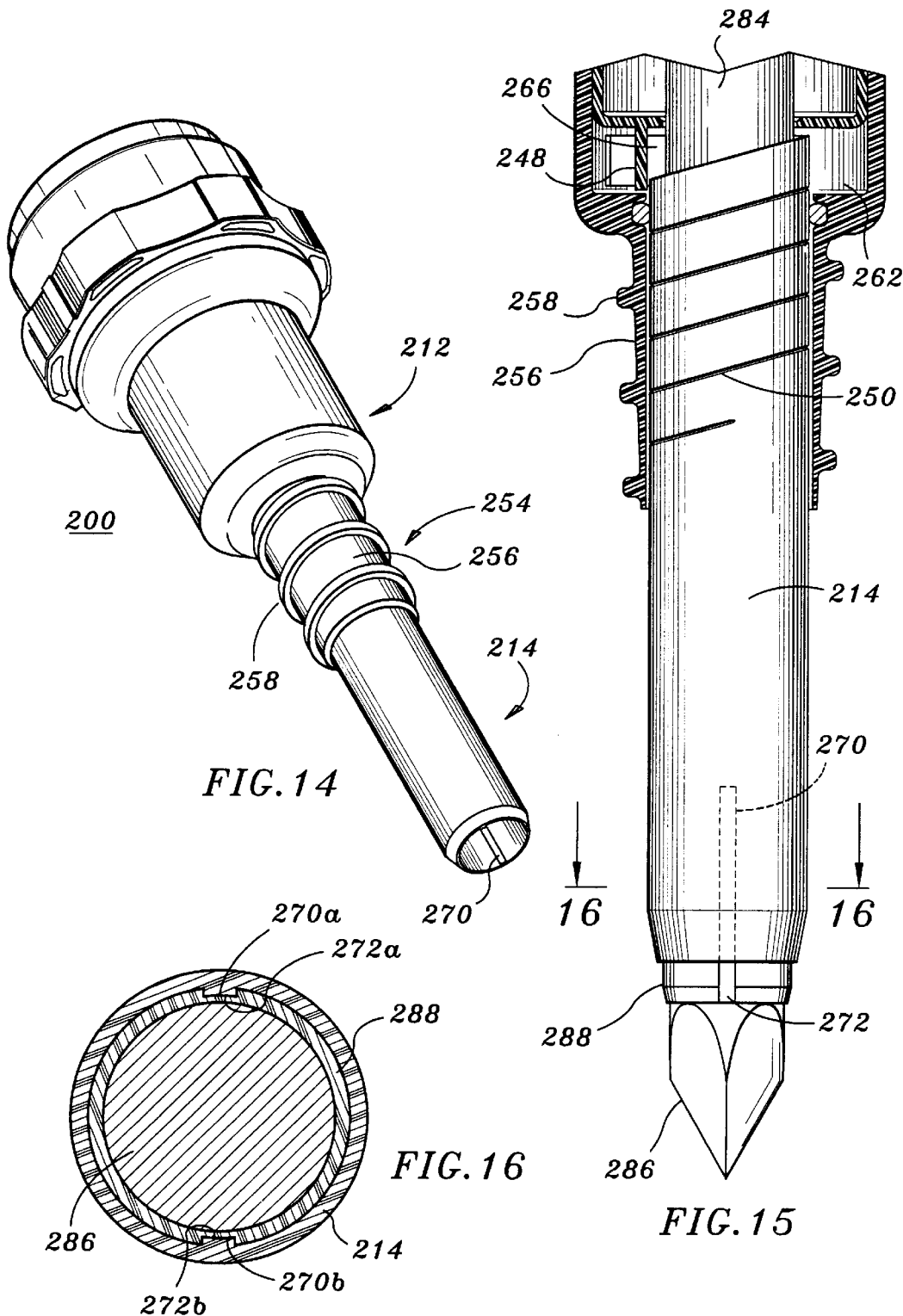

SURGICAL CANNULA HAVING A VARIABLE LENGTH

BACKGROUND

1. Technical Field

The present disclosure relates to cannula assemblies which are adapted to allow the introduction of a surgical instrument into a patient's body. In particular, the disclosure relates to cannula assemblies having a cannula configured to be shortenable from a first length to a second length.

2. Background of Related Art

Laparoscopic procedures are performed in the interior of the abdomen through a small incision, e.g., through narrow endoscopic tubes or cannulas inserted through a small entrance incision in the skin. Minimally invasive procedures performed elsewhere in the body, e.g., in the chest, are often generally referred to as "endoscopic" procedures. Minimally invasive or endoscopic procedures generally require that any instrumentation inserted into the body be sealed, i.e. provisions must be made to ensure that gases do not enter or exit the body through the endoscopic incision as, for example, in surgical procedures in which the surgical region is insufflated. Moreover, endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a system incorporating a trocar and cannula assembly. A cannula assembly is formed of a cannula attached to a cannula housing which generally includes a valve assembly adapted to maintain a seal across the opening of the valve assembly both with and without an instrument inserted therethrough. Since the cannula is in direct communication with the internal portion of the valve assembly, insertion of the cannula into an opening in the patient's body so as to reach the inner abdominal cavity should be adapted to maintain a fluid tight interface between the abdominal cavity and the outside atmosphere.

Since minimally invasive surgical procedures in the abdominal cavity of the body generally require insufflating gases to raise the cavity wall away from vital organs, the procedure is usually initiated by use of a Verres needle through which a gas is introduced into the body cavity. The gas provides a slight pressure which raises the wall surface of the peritoneum away from the vital organs thereby providing an adequate region in which to operate. Thereafter, a trocar assembly which includes a trocar or obturator is inserted within the cannula to puncture the peritoneum, i.e. the inner lining of the abdominal cavity wall. The obturator is removed and laparoscopic or endoscopic surgical instruments may then be inserted through the cannula to perform surgery within the abdominal cavity. The cannula may also be utilized for introducing tubes into the body as for drainage purposes, for specimen removal, for diagnostic evaluations, or the like.

In view of the need to maintain the atmospheric integrity of the inner area of the cavity, a valve assembly for a cannula which permits introduction of an obturator and a wide range of surgical instruments and which maintains the atmospheric integrity of the inner area of the cavity is desirable. A particularly suitable valve assembly is disclosed in commonly-assigned, copending U.S. patent application Ser. No. 08/287,395, filed Aug. 8, 1994 by Smith et al., the contents of which are hereby incorporated by reference. This valve assembly is capable of forming and maintaining a tight seal about instruments of varying diameters inserted through the cannula and incorporates structure to enhance and facilitate passage of the instrument through the valve unit.

In addition, it is also desirable to maintain the position of the cannula assembly within the body tissue during the surgical procedure. In particular, the position of the cannula assembly may be disturbed by the insertion and removal of surgical instrumentation, as well as the manipulation thereof within the body cavity.

U.S. Pat. No. 5,002,557 to Hasson, for example, suggests a cannula assembly having a sleeve which may be inserted into a body cavity. The sleeve includes expandable structure at a distal end thereof to prevent withdrawal of the sleeve. A retaining collar is movable relative to the sleeve to capture tissue between the collar and the expandable structure to maintain the sleeve in position.

U.S. Pat. No. 5,290,249 to Foster et al. disclose a retention mechanism for a cannula assembly inserted through the abdominal wall. A plurality of laterally expanding retention strips engage the interior surface of the abdominal wall, and a retention dish engages the external surface of the abdominal wall in order to stabilize the cannula assembly.

A limitation of known cannula assemblies concerns the substantial length of the cannula. The length of the cannula is generally selected to span a range of anatomies and may, in certain instances, be influenced by the retention mechanism which may be slidably mounted on the cannula to positively secure the cannula to body tissue. Consequently, the portion of the cannula assembly which extends above the body cavity may be greater than otherwise desired.

A need exists, therefore, for a cannula assembly which facilitates introduction of instruments to a surgical site, while minimizing the profile of the cannula assembly above the body wall to the extent possible.

SUMMARY

The present disclosure is directed to a cannula assembly for insertion through body tissue which includes a housing and a cannula having a proximal end portion and a distal end portion. The cannula is supported at the proximal end portion by the housing and has a first, predetermined length and is shortenable to a second, predetermined length with respect to the housing. The preferred cannula assembly includes a cutting member to remove a proximal portion of the cannula. The housing can be mounted for axial rotation with respect to the cannula. The cutting member which can be disposed on the housing is configured to detach portions of the cannula in response to relative axial rotation of the housing with respect to the cannula. A portion of the cannula has a helical scoring formed thereon to facilitate removal of portions of the cannula. The housing defines a cavity for storing portions of the cannula which are removed by the cutting member.

The cannula assembly may further include an anchor disposed on the cannula. In a preferred form, the anchor is an inflatable collar disposed on the distal end portion of the cannula. The housing and the anchor are relatively movable with respect to the cannula in order to secure body tissue secured between the housing and the anchor. In another preferred form, the anchor is a helical threaded portion associated with the housing.

These and other features of the cannula assembly will become more readily apparent to those skilled in the art from the following detailed description of preferred embodiments of the present disclosure.

BRIEF DESCRIPTION OF THE DRAWINGS

Various embodiments are described hereinbelow with reference to the drawings, wherein:

FIG. 4 is a side elevational view in partial cross-section of the cannula assembly of FIG. 1, illustrating the cannula at an initial length;

FIG. 5 is a cross-sectional view of the housing taken along section line 5—5 of FIG. 4, illustrating the cutting member and the cannula;

FIG. 9 is a side elevational view in partial cross section corresponding to the relative positions of the housing and the anchor shown in FIG. 8;

FIG. 10 is a cross-sectional view of the housing taken along section line 10—10 of FIG. 9 illustrating the storage of the cannula sections within the housing;

FIG. 11 is a perspective view of a cannula assembly constructed in accordance with another preferred embodiment, illustrating a gripping member for releasably securing a tool assembly inserted therein;

FIG. 14 is a perspective view of another preferred embodiment of the cannula assembly illustrating an alternative anchor assembly;

FIG. 15 is a side elevational view in partial cross-section of the cannula assembly of FIG. 14 and an obturator inserted therethrough; and FIG. 16 is a cross-sectional view of the cannula and obturator taken along section line 16—16 of FIG. 15, illustrating the locking assembly for simultaneous coaxial movement of the cannula and obturator.

DETAILED DESCRIPTION OF PREFERRED EMBODIMENTS

Figure 1:
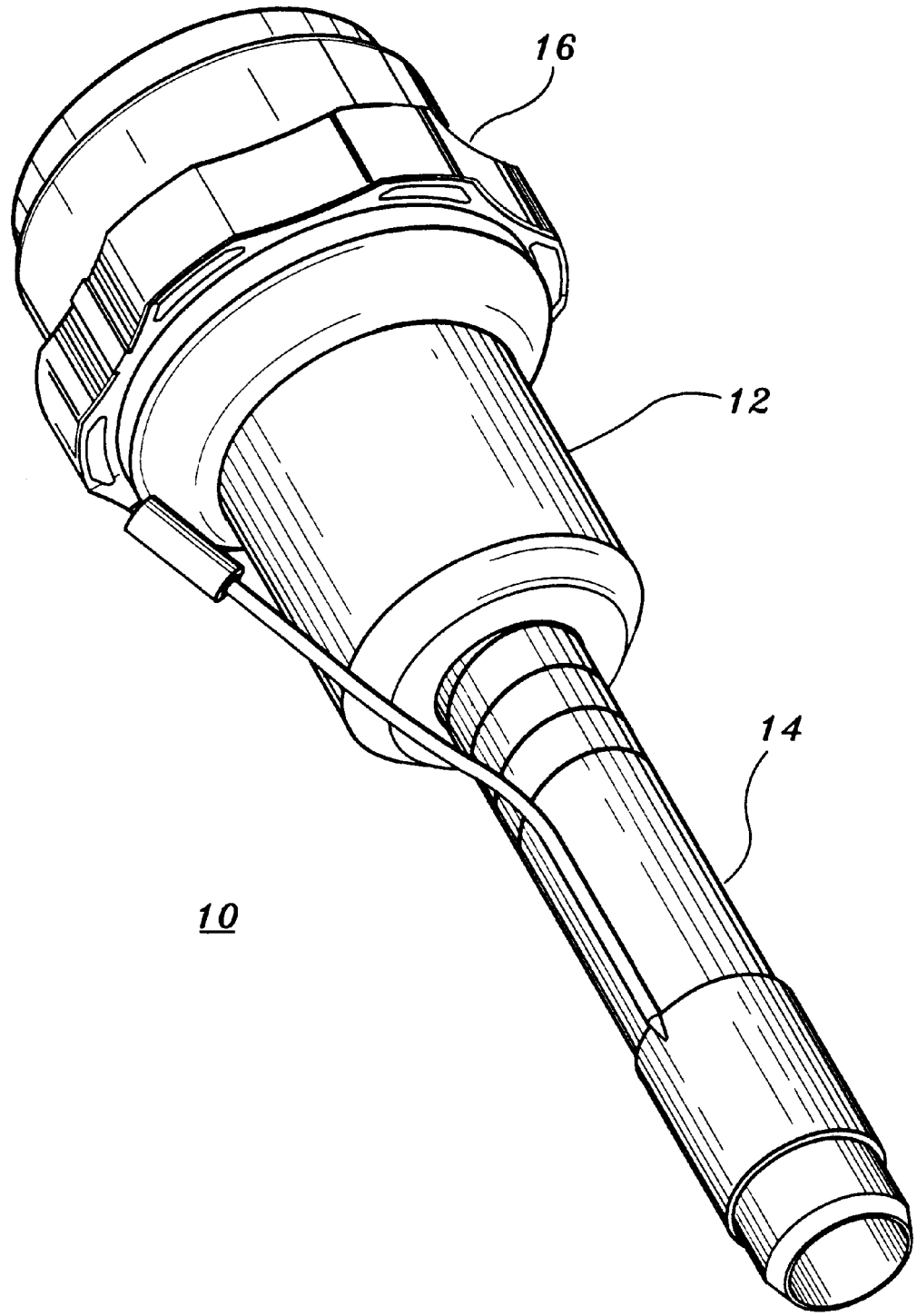
FIG. 1 is a perspective view of a cannula assembly constructed in accordance with a preferred embodiment of the present disclosure.

In the drawings and in the description which follows, the term "proximal", as is traditional, will refer to the end of the apparatus which is closest to the operator, while the term "distal" will refer to the end which is furthest from the operator.

The present disclosure contemplates the introduction into a body cavity of all types of surgical instruments including clip appliers, graspers, dissectors, retractors, staplers, laser fibers, photographic devices, endoscopes and laparoscopes, tubes, and the like. All such objects are referred to herein as "instruments".

Referring initially to FIG. 1, there is illustrated a cannula assembly 10 constructed in accordance with the principles of the present disclosure. Cannula assembly 10 includes housing 12, which supports cannula sleeve 14 at a distal portion and valve assembly 16 at a proximal portion thereof. Cannula sleeve 14 is configured to be shortenable from a first predetermined length to a second predetermined length.

Figure 2:
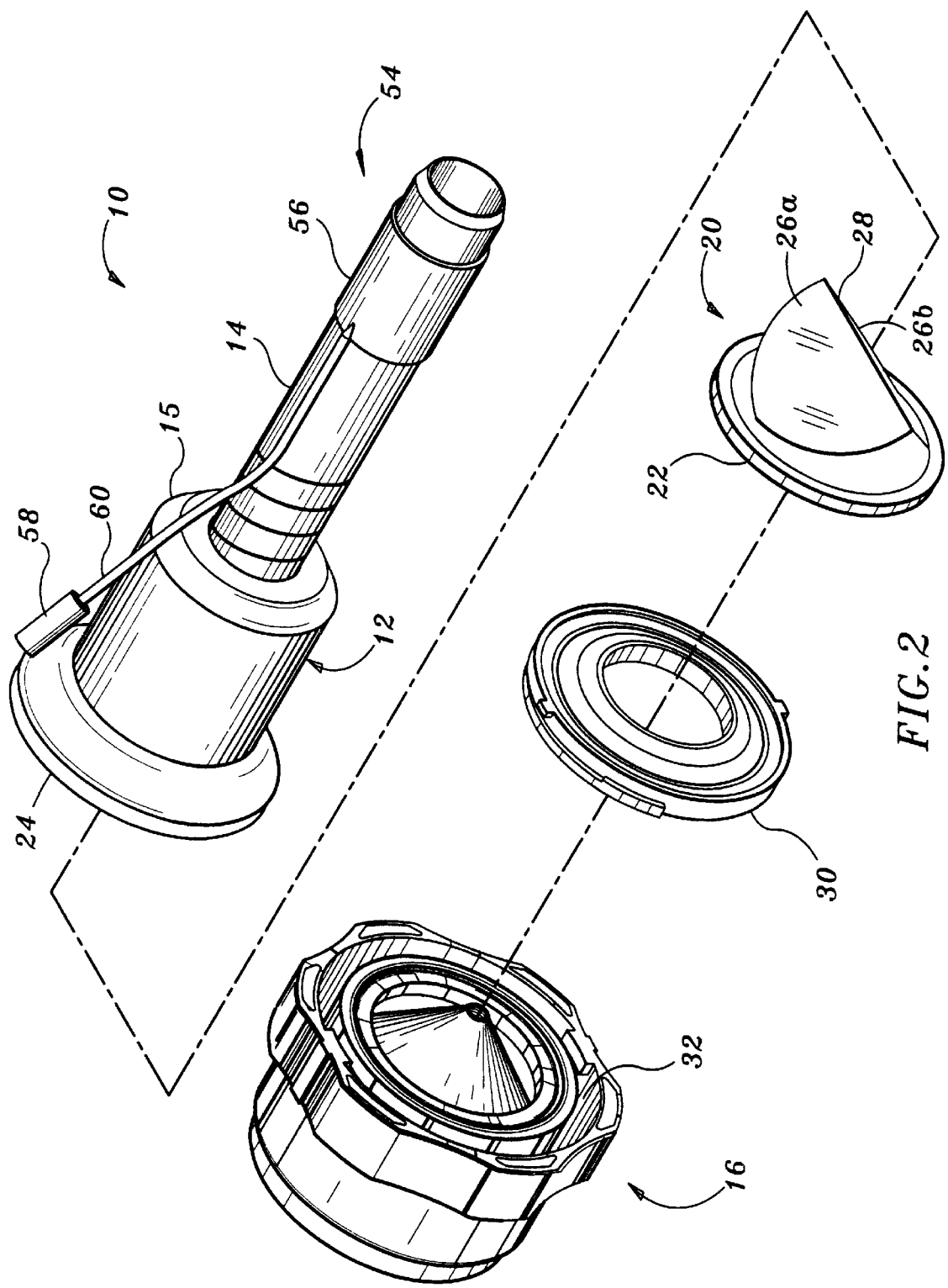
FIG. 2 is a perspective view of the cannula assembly of FIG. 1, with the valve assembly parts separated.

Referring now to FIG. 2, valve assembly 16 provides a substantial fluid-tight seal between a body cavity of a patient and the outside atmosphere, both during and subsequent to insertion of an instrument through the cannula assembly 10. Valve assembly 16 is preferably detachably mounted to a proximal end of housing 12 disclosed herein. Thus, a surgeon can remove valve assembly 16 from cannula assembly 10 at any time during the surgical procedure and, similarly mount the valve assembly 16 to the cannula assembly when desired to provide a sealing engagement with appropriately sized instruments to be inserted through the cannula. The detachability of valve assembly 16 from housing 12 reduces the profile of cannula assembly 10 when valve assembly is not needed for the particular surgical procedure. Additionally, removal of valve assembly 16 permits objects, e.g., tissue to be removed, etc., to pass more readily through the larger diameter opening formed in cannula housing 12.

Cannula valve seal 20 is fabricated from a resilient material, e.g. rubber, and is positioned within the interior of cannula housing 12. Valve 20 includes a circumferential flange portion 22 which rests on a correspondingly dimensioned circumferential ledge 24 within cannula housing 12. valve 20 is in the form of a "duck-bill" valve and generally defines two planar tapering flap portions 26a, 26b which intersect at their distal ends to define an abutment face opening 28. The planar tapering flap portions 26a, 26b may each include one or more inwardly directed, longitudinally oriented ribs to facilitate instrument passage. Abutment face opening 28 permits passage of an elongated object through the valve 20, but in the absence of an instrument, and particularly when cannula 14 is inserted into an insufflated body cavity, abutment face opening 28 is forced to a closed position due to the pressure exerted by the insufflated gases, thereby forming a fluid-tight seal between the insufflated cavity from the ambient surroundings.

Cannula assembly 10 also includes a stabilizing plate 30 which is securely mounted to the flange portion 22 of valve 20 to maintain the positioning of and provide support for valve 20 during introduction and withdrawal of an elongated instrument. Stabilizing plate 30 is securely attached to cannula housing 12 at contact points along the extensions of the respective components by spot welding, adhesives or the like.

The assembled valve assembly 16 is detachably mounted adjacent stabilizing plate 30 with a portion of the stabilizing plate being received within peripheral groove 32 defined in the distal face of valve assembly 16. The valve assembly 16 may be detachably mounted to the housing 13 by screw threads, adhesives, or bayonet-type mount locking, etc. A stop cock valve (not shown) may be incorporated in cannula housing 12 to permit the passage of insufflation gases through the cannula and into the body cavity.

Figure 3:
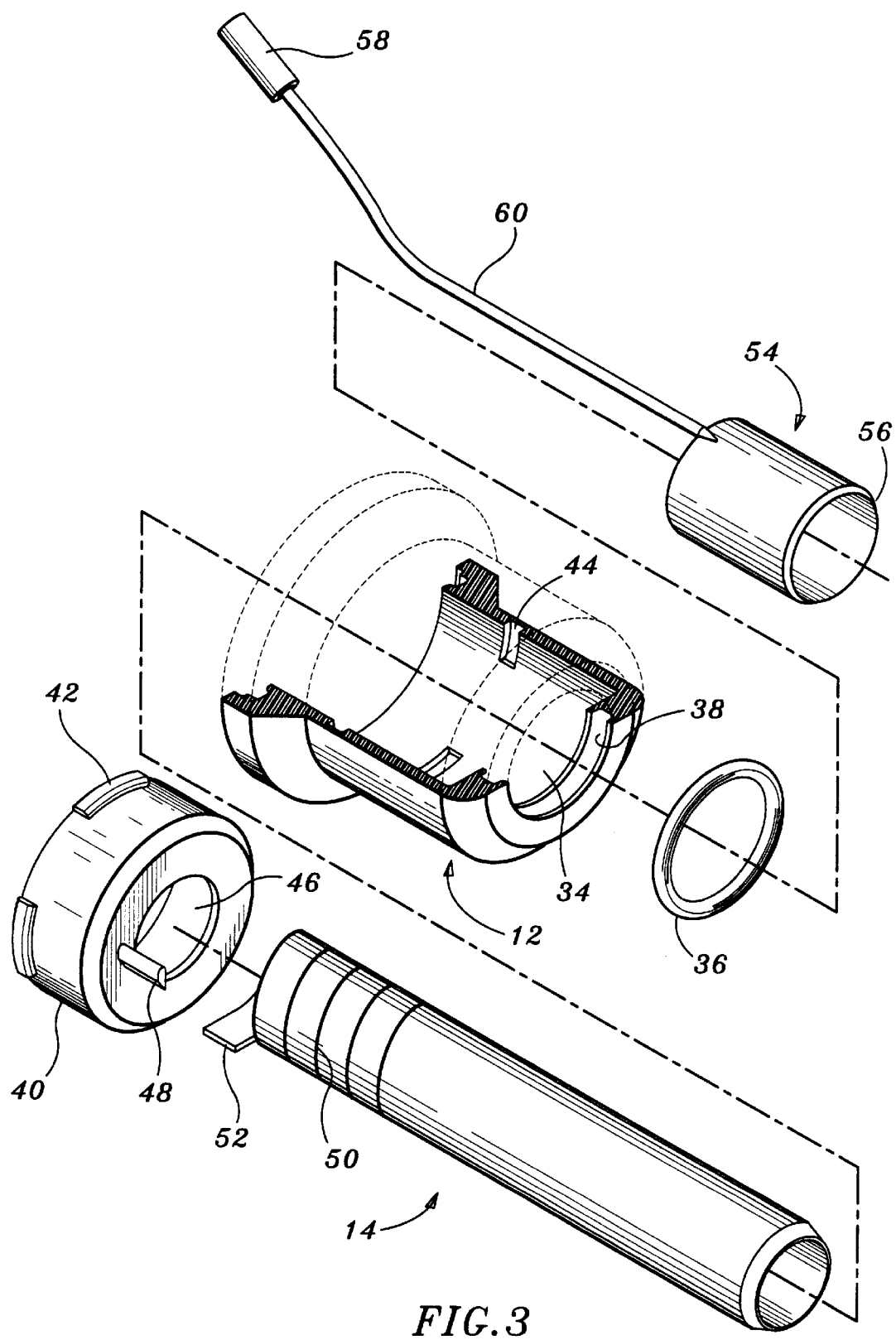
FIG. 3 is a perspective view with parts separated of the cannula assembly of FIG. 1 illustrating the housing, the cannula, and the anchor.

Referring now to FIG. 3, housing 12 supports cannula sleeve 14 at a proximal portion thereof. The distal portion of cannula sleeve 14 passes through aperture 34 and is held in place by a seal, such as O-ring 36, which is fitted within annular groove 38 in housing 12 to maintain insufflation. The diameter and resilient characteristics of O-ring 36 will be selected as is known in the art to support cannula sleeve 14 to permit relative longitudinal displacement and axial rotation of housing 12 while inhibiting slippage or unintended movement as will be described below.

Collar 40 is mounted within the interior of housing 12 and fixedly secured therein by tabs 42 disposed within recesses 44 on housing 12 or by any other suitable known attaching methods. Collar 40 includes aperture 46 for accommodating instruments passing therethrough and supports a cutting member 48. Alternatively, cutting member 48 can be directly supported by housing 12 and collar 40 eliminated.

Cannula sleeve 14 includes a helical scoring 50 formed partially through the thickness of sleeve 14. Scoring 50 terminates adjacent the proximal end of sleeve 14, forming a tab 52. Cutting member 48 is dimensioned to cooperate with tab 52 and engage helical scoring 50 to remove a proximal portion of sleeve 14 as will be described herein.

Figure 8:
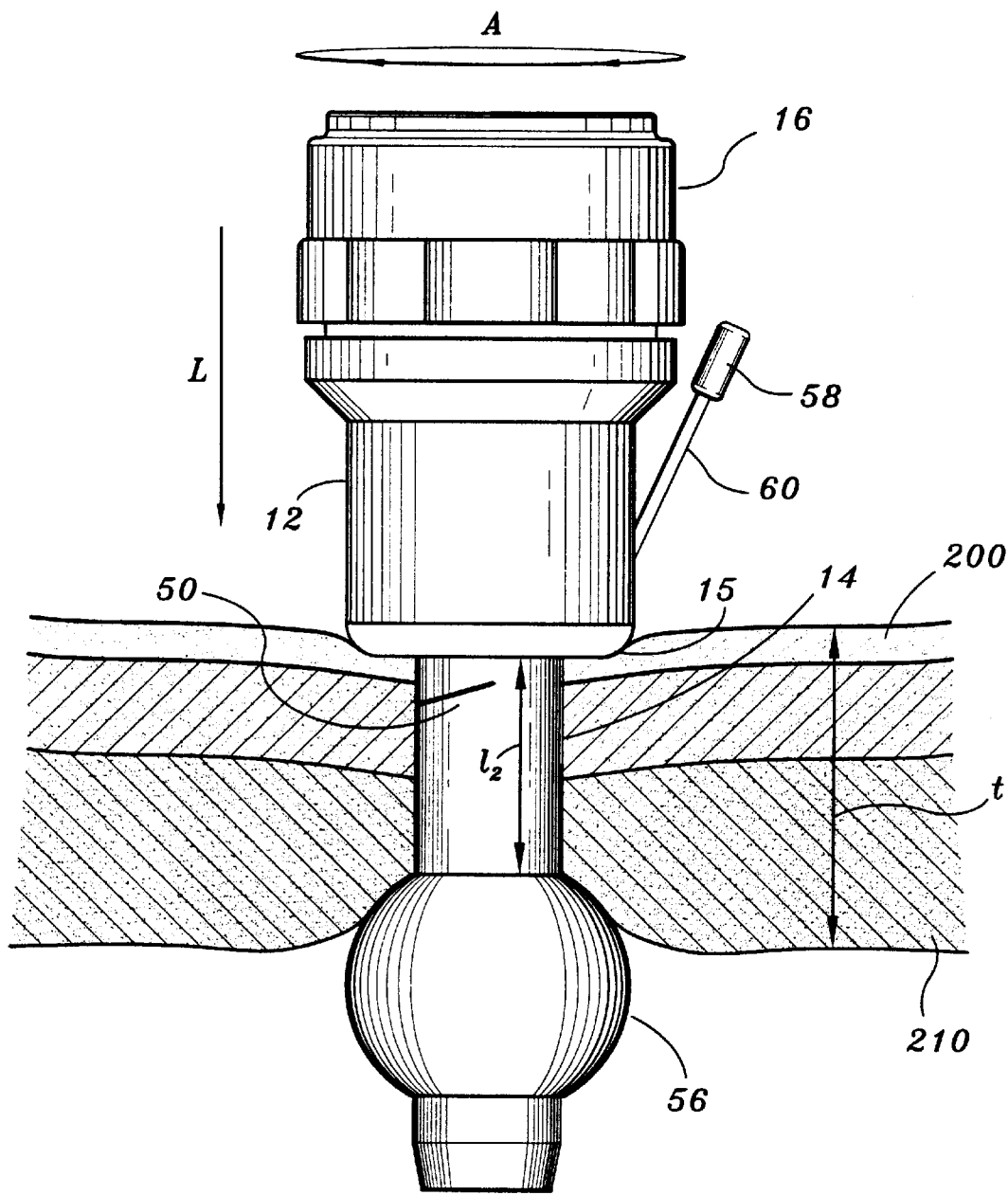
FIG. 8 is a side elevational view of the cannula assembly inserted through body tissue, illustrating the cannula at a second length, the anchor in an expanded configuration, and the body tissue disposed between the housing and the expanded anchor collar.

Anchor assembly 54 is disposed at the distal portion of sleeve 14 and includes a pneumatically expandable collar 56 which is configured to move from a collapsed or uninflated configuration (shown), to an expanded or inflated configuration (See, e.g. FIGS. 8–9). Collar 56 can be formed from an elastic material such as rubber or a polymer. Preferably, a one-way valve 58 and supply tube 60 supply gas to expand collar 56 or to evacuate gas therefrom. Supply tube 60 is preferably flexible and configured to maintain a low profile alongside sleeve 14 during insertion through body tissue.

Turning now to FIGS. 4–5, with initial reference to FIG. 4, the placement of collar 40 within housing 12 creates a cavity or recess 62 at the distal portion of housing 12 adjacent the proximal end portion of cannula sleeve 14. Cutting member 48, disposed on collar 40, engages tab 52 which extends partially into cannula recess 62. As illustrated in FIG. 5, cannula recess 62 has a substantially annular configuration for receiving the proximal portion of sleeve 14 as it is removed by cutting member 48. In order to inhibit sleeve from sliding proximally and to provide longitudinal force on the sleeve during insertion into the body cavity, aperture 46 in collar 40 can be sized smaller than the outer diameter of sleeve 14.

With continued reference to FIG. 4, cannula sleeve 14 has a predetermined length "$1_1$" as defined between the distal portion 15 of housing 12 and the proximal end of expandable collar 56. Length "$1_1$" is experimentally determined to provide sufficient clearance between body tissue and housing 12 and expandable collar 56 during insertion and preliminary adjustments of cannula assembly 10 prior to shortening of cannula sleeve 14 described hereinbelow.

Figure 6:
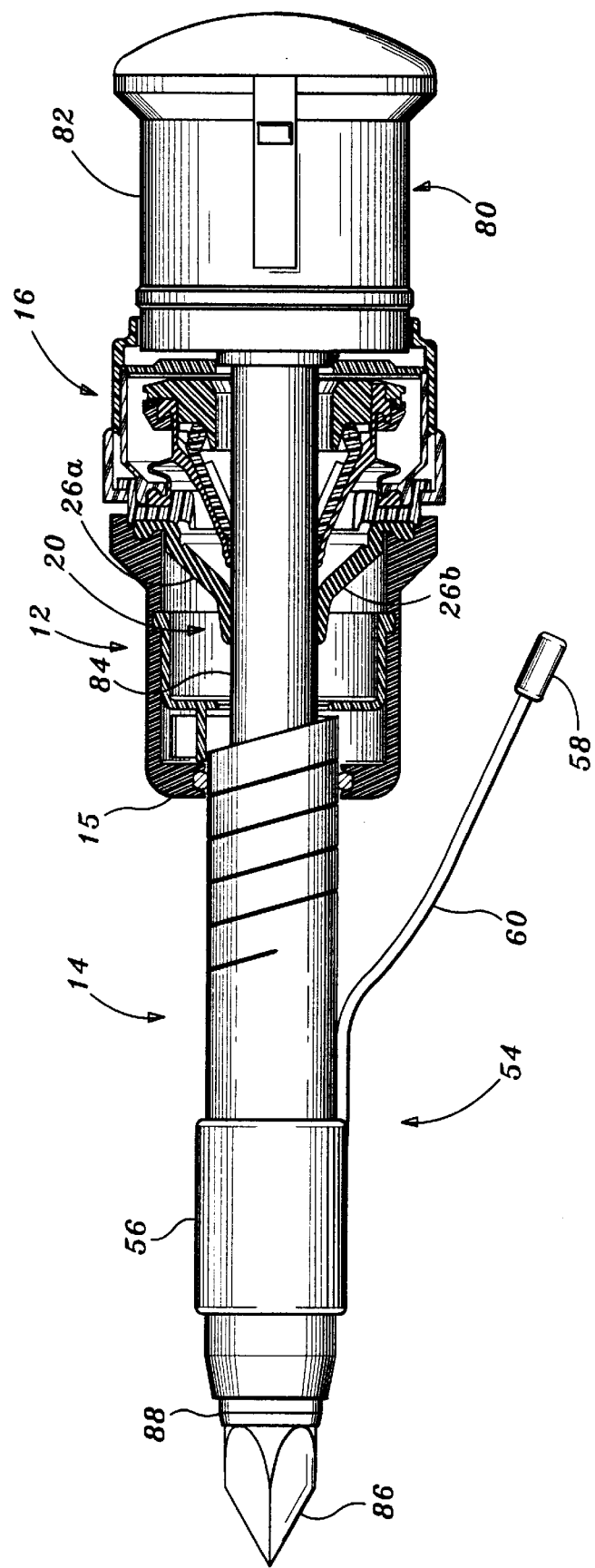
FIG. 6 is a side elevational view in partial cross-section of the cannula assembly of FIG. 1 and an obturator rod inserted therethrough, illustrating the orientation of the valve assembly to accommodate the obturator rod.

FIG. 6 illustrates cannula assembly 10 of the present disclosure with trocar assembly 80 inserted therethrough for penetration of body tissue. A suitable exemplary trocar assembly is disclosed in commonly-assigned U.S. Pat. No. 5,356,421 to Castro, the contents of which are hereby incorporated by reference. Trocar assembly 80 includes trocar housing 82 to be gripped by the surgeon and obturator 84 extending distally from trocar housing 82. Piercing tip 86 is disposed at the distal end of obturator 84. Outer tube 88 houses obturator 84 and surrounds piercing tip 86 when obturator 84 is unarmed to prevent unintended piercing of tissue. Obturator 84 is inserted within an aperture defined in valve assembly 16 and advanced through seal 20 and into cannula sleeve 14. In order to expose the piercing tip 86, obturator 84 is further advanced beyond the distal end of cannula sleeve 14. Trocar housing 82 can be longitudinally fixed with respect to valve assembly 16 and cannula assembly 10 by a known releasable mount such as a bayonet mount.

Figure 7:
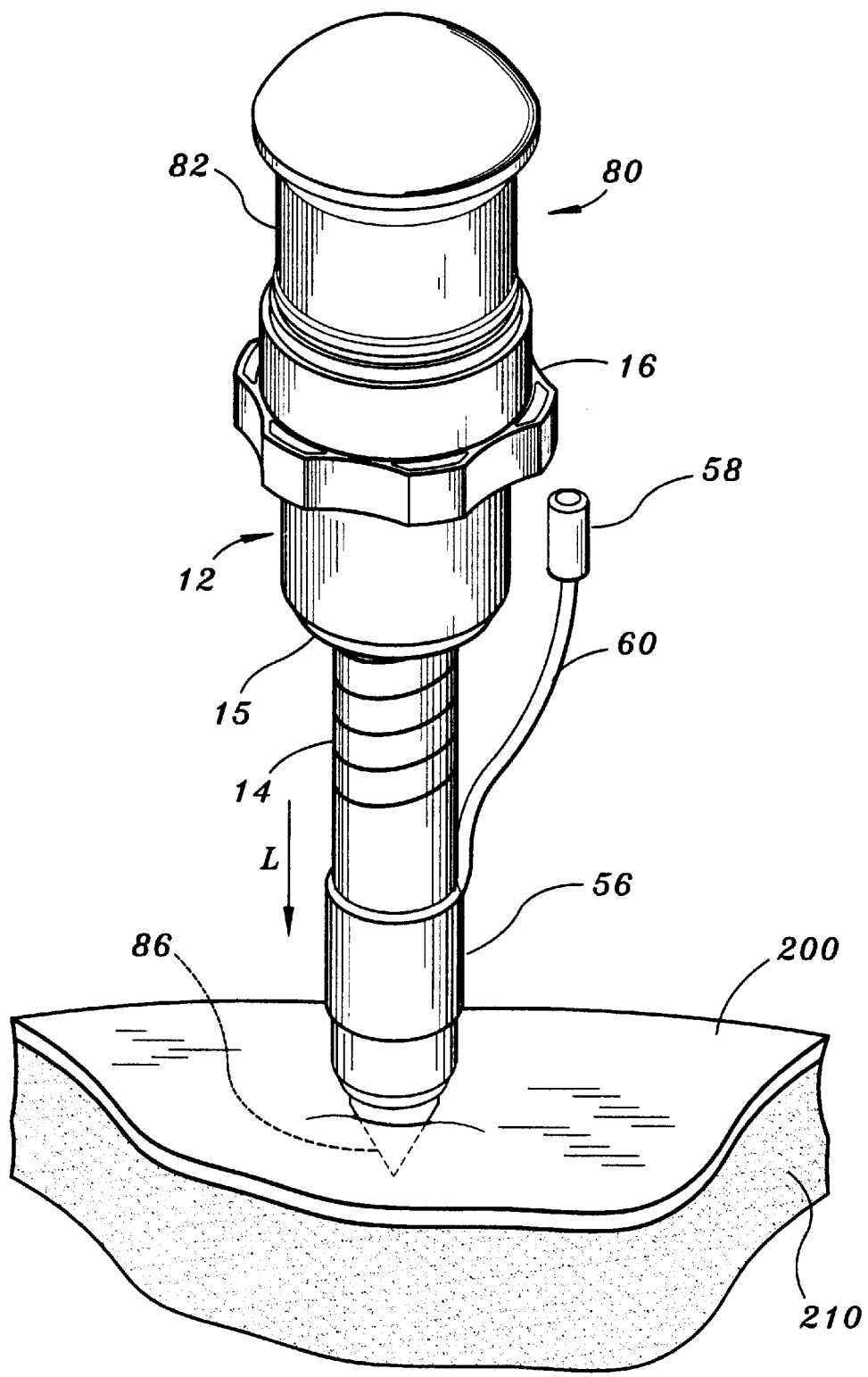
FIG. 7 is a perspective view of the cannula assembly and the obturator rod of FIG. 6 illustrated during initial penetration of a body cavity.

Referring now to FIG. 7, the distal end of obturator 84 having the piercing tip 86 (illustrated in phantom) in an exposed position beyond cannula sleeve 14 is placed against the skin 200 at the body cavity region, and pressure is exerted on the assembly 10 against the skin 200 in the direction of arrow "L". This pressure causes the piercing tip 86 to enter the skin 200 and underlying tissue 210, such as the peritoneum of the abdominal wall. Once the tip 86 has penetrated the tissue and has entered the cavity, the tip automatically retracts into the cannula as described in U.S. Pat. No. 5,116,353 to Green, the contents of which are hereby incorporated by reference. The cannula sleeve 14 is further inserted through body tissue 210 with collar 56 in a retracted or non-inflated state to a depth in which collar 56 is partially disposed within the operative body cavity (See, FIG. 8). Trocar assembly 80 can subsequently be withdrawn from cannula assembly 10 to permit the introduction of surgical instruments such as forceps, graspers, and the like through cannula sleeve 14. Upon removal of trocar assembly 80 from cannula assembly 10, duck bill valve 20 closes to maintain the insufflation of the body cavity.

Referring now to FIG. 8, cannula assembly 10 is secured to body tissue 210, which is pinched or compressed between collar 56 and cannula housing 12. A known external supply (not shown) provides a fluid such as gas, which enters one-way valve 58 and flows through supply tube 60 to expand the inflatable collar 56. With collar 56 disposed as illustrated in FIG. 8, an upward pinch or compressive force is imposed on body tissue 210 by the expanded collar 56. Downward compression is provided on body tissue 210 by the distal edge 15 of cannula housing 12, which is mounted for both longitudinal movement and axial rotation with respect to cannula sleeve 14. Rotation of cannula housing in the direction of arrow "A" removes or strips away a proximal portion of cannula sleeve 14 as described below, thereby conveying cannula housing 12 longitudinally with respect to sleeve 14 in the direction of arrow "L". The longitudinal movement of cannula housing reduces the distance between housing 12 and collar 56 from the first length "$1_1$" (FIG. 4) to a second length "$1_2$," which is smaller than the thickness "t" of body tissue 210. The pinch applied to body tissue 210 by cannula housing 12 and collar 56 stabilizes cannula assembly 10 with respect to body tissue 210 and inhibits leakage or escape of insufflation gases from the incision.

With reference to FIGS. 9 and 10, the approximation of cannula housing 12 and inflatable collar 56 is effectuated by the removal of proximal portions of cannula sleeve 14. As illustrated in FIGS. 4–5, cutting member 48 is initially disposed adjacent tab 52. Axial rotation of housing 12 in the direction of arrow "A" brings cutting member 48 into engagement with cannula sleeve 14. More particularly, cutting member 48 applies a force to sleeve 14 adjacent helical scoring 52 which is sufficient to separate a strip 66 from the sleeve 14. Further rotation of housing 12 facilitates continued removal of strip 66 from sleeve 14, which is subsequently stored in recess 62, as shown in FIG. 10. The depth of helical scoring 50 is sufficient to allow separation of strip 66 upon engagement with cutting member 48 without degrading the strength of sleeve 14. Simultaneous with the removal of strip 66, housing 12 is displaced longitudinally toward collar 56. As illustrated in FIG. 8, the distal edge 15 of housing 12 is curved to permit pressure to be placed on skin 200 and body tissue 210 atraumatically.

Figure 13:
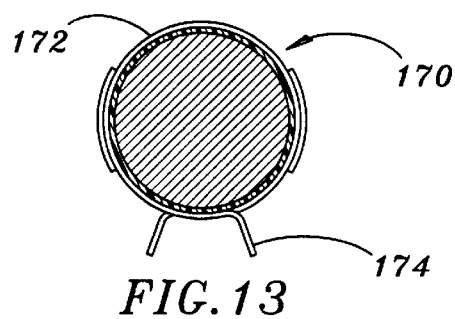
FIG. 13 is a cross-sectional view of the gripping member associated with the housing, taken along section line 13—13 of FIG. 12.

Turning now to FIG. 11, there is illustrated another preferred embodiment of the subject cannula assembly, designated generally at 100. Cannula assembly 100 includes cannula sleeve 114 depending from housing 112. Anchor assembly 154 is provided at the distal end portion of sleeve 114. Anchor assembly 154 includes expandable collar 156, which is supplied with a fluid, e.g., a gas, at one-way valve 158 and through supply tube 160. Surgical instruments can be inserted into sleeve 114 at distal aperture 180. Locking assembly 170, provided at the proximal portion of housing 112 is configured to releasably secure such surgical instruments with respect to housing 112. Referring to FIG. 13 in conjunction with FIG. 11, locking assembly 170 includes a resilient collar 172 sized to restrain instruments in its normally biased position, and a pair of finger tabs 174 to bias collar 172 to an expanded configuration to facilitate insertion and removal of surgical instrumentation therefrom.

Figure 12:
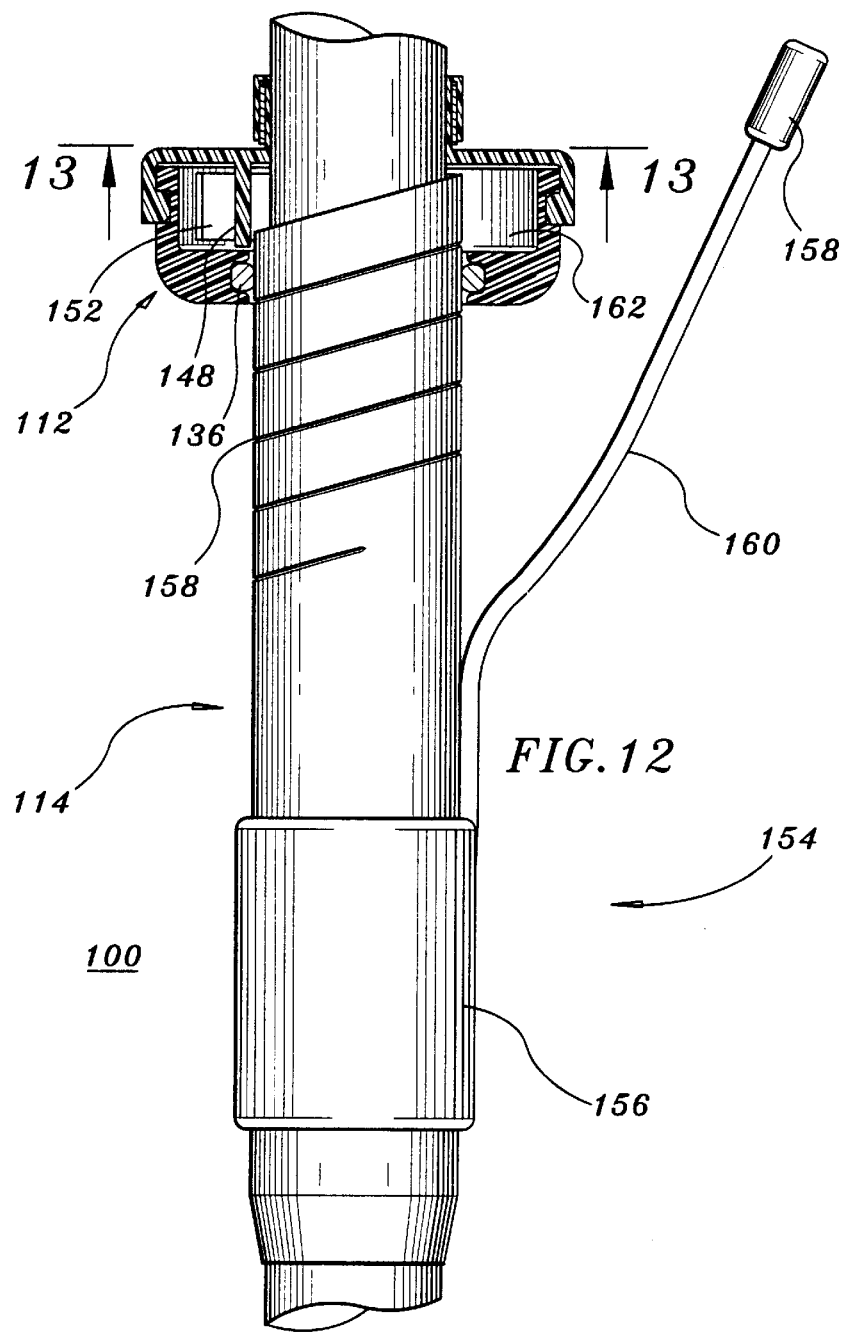
FIG. 12 is a side elevational view in partial cross-section of the cannula assembly of FIG. 11.

As illustrated in FIG. 12, housing 112 of cannula assembly 100 is configured to shorten cannula sleeve 114 substantially as described above with respect to cannula assembly 10. Housing 112 is mounted for axial rotation and longitudinal displacement with respect to sleeve 114. O-ring seal 136 is disposed between cannula sleeve 114 and housing 112 to provide stability to assembly 100 and sufficient resistance to inhibit slippage or unintended rotation or longitudinal displacement. Cutting member 148 is disposed adjacent the proximal end of sleeve 14. Rotation of housing 112 about sleeve 114 enables cutting member 148 to progressively remove the proximal portion of sleeve 114. In particular, cutting member 148 engages sleeve 114 adjacent helical scoring 150 to separate a proximal strip which is stored in recess 162 in housing 112. Progressive rotation of housing 112 and removal of a proximal portion of sleeve 114 permits housing 112 to be approximated with anchor 154 to secure cannula assembly 100 to body tissue, in the manner shown with regard to cannula assembly 10 in FIG. 8.

Turning to FIGS. 14–16, with initial reference to FIG. 14, there is shown another preferred embodiment of the subject cannula assembly, designated generally by reference numeral 200. Cannula assembly 200 includes cannula sleeve 214 and housing 212 rotatable and longitudinally movable with respect thereto. Anchor assembly 254 is associated with housing 212, and includes a tube 256 depending from housing 212, and helical threading 258 formed on an outer surface thereof for engagement with body tissue during insertion of cannula sleeve 214.

Cannula assembly 200 is configured to permit simultaneous rotation about the longitudinal axis of cannula sleeve 214 and trocar assembly 280. FIG. 14 illustrates a longitudinal rib or tab 270 formed on the inner surface of cannula sleeve 214. Longitudinal rib 270 (shown in phantom in FIG. 15) is dimensioned and configured to engage longitudinal groove or keyway 272 formed on the surface of outer tube 288 of obturator 284. As illustrated in FIG. 16, cannula sleeve 214 can include two or more ribs 270a, 270b to interlock with grooves 272a, 272b to facilitate simultaneous rotation of cannula sleeve 214 and trocar assembly 280.

With continued reference to FIG. 15, cannula housing 212 includes a cutting member 248 configured to engage the proximal portion of cannula sleeve 214 to remove a proximal portion thereof. In particular, axial rotation of cannula housing 212 directs cutting member 248 to separate the cannula sleeve 214 along helical scoring 250 into strip 266. Continued rotation of housing 212 facilitates removal of strip 266 from sleeve 214, which is stored in recess 262 of housing 212. As a proximal portion of sleeve 214 is removed, housing 212 is displaced longitudinally downward, effectively reducing the length of cannula sleeve 214.

In use, obturator 284 is inserted in cannula sleeve 214, in order to engage rib 270 with keyway 272. By applying pressure to body surface, piercing tip 286 is first exposed from outer tube 288 to penetrate body tissue and subsequently retracted. Cannula housing 212 is axially rotated to drive threads 258 into body tissue to secure cannula assembly 200 thereto. Shortening of cannula sleeve 214 is facilitated by rib 270 and keyway 272. In order to permit relative rotation of housing 212 and cutting member 248 with respect to cannula sleeve 214, cannula sleeve 214 is held stationary by gripping trocar housing 82 (See, FIG. 6) cannula housing 212 is rotated.

It will be understood that various modifications may be made to the embodiments shown herein. For example, the spacing and depth of the helical scoring may be modified to suit the materials selected for the cannula sleeve and cutting member. Therefore, the above description should not be construed as limiting, but merely as exemplifications as preferred embodiments. Those skilled in the art will envision other modifications within the scope and spirit of the claims appended hereto.

What is claimed is:

1. A cannula assembly for insertion through tissue, comprising:

a housing defining a longitudinal bore and movably mounted to a cannula having a proximal end portion, a distal end portion, and defining a longitudinal bore aligned with the longitudinal bore in the housing, a cutting member mounted in the housing for cutting engagement with the proximal portion of the cannula, the housing movable between a first predetermined position and a second predetermined position relative to the cannula.

2. The cannula assembly of claim 1, wherein the cutting member is configured to remove a proximal portion of the cannula to shorten the cannula as the housing is moved between the first predetermined position and the second predetermined position.

3. The cannula assembly of claim 1, wherein the housing is mounted for axial rotation with respect to the cannula.

4. The cannula assembly of claim 3, wherein the cutting member is configured to detach portions of the cannula in response to relative axial rotation of the housing with respect to the cannula.

5. The cannula assembly of claim 4, wherein the housing defines a cavity for storing the portions of cannula removed by the cutting member.

6. The cannula assembly of claim 1, wherein at least a portion of the cannula has a helical scoring formed thereon to facilitate removal of portions of the cannula.

7. The cannula assembly of claim 1, further comprising a seal member disposed between the housing and the cannula.

8. A cannula assembly for insertion through tissue into a body cavity which comprises:

a) a housing defining a longitudinal bore and movably mounted to a cannula having a proximal end portion, a distal end portion, and defining a longitudinal bore aligned with the longitudinal bore in the housing, a cutting member mounted in the housing for cutting engagement with the proximal portion of the cannula, the housing movable between a first predetermined position and a second predetermined position relative to the cannula; and b) an anchor disposed on the cannula, wherein the anchor is movable between a first configuration to facilitate introduction of the cannula assembly into such body cavity and a second configuration to facilitate retention of the cannula assembly in a predetermined position relative to such body cavity.

9. The cannula assembly of claim 8, wherein the cutting member is configured to remove a proximal portion of the cannula to shorten the cannula as the housing is moved between the first predetermined position and the second predetermined position.

10. The cannula assembly of claim 8, wherein the housing is mounted for axial rotation with respect to the cannula.

11. The cannula assembly of claim 10, wherein a cutting member is disposed on the housing and is configured to detach portions of the cannula in response to relative axial rotation of the housing with respect to the cannula.

12. The cannula assembly of claim 11, wherein the housing defines a cavity for storing the portions of the cannula removed by the cutting member.

13. The cannula assembly of claim 8, wherein at least a portion of the cannula has a helical scoring formed thereon.

14. The cannula assembly of claim 8, which further comprises a seal member disposed between the housing and the cannula.

15. The cannula assembly of claim 8, wherein the anchor includes an expandable collar disposed at the distal end portion of the cannula.

16. The cannula assembly of claim 8, wherein the anchor includes helical threading associated with the housing.

17. The cannula of claim 16, wherein the cannula includes at least one tab at the proximal end portion.

18. The cannula assembly of claim 17, which further comprises an obturator rod defining at least one groove for receiving the tab on the cannula.

19. A cannula assembly for insertion through body tissue comprising:
   a) a housing defining a longitudinal bore and having a cutting member, the housing being movably mounted to a cannula having a proximal end portion, a distal end portion, and defining a longitudinal bore aligned with the longitudinal bore in the housing, the cutting member mounted in the housing for cutting engagement with the proximal portion of the cannula, the housing movable between a first predetermined position and a second predetermined position relative to the cannula; and
   b) an anchor disposed adjacent the distal end portion of the cannula, the anchor and the housing mounted for relative movement to stabilize the cannula with respect to such body tissue gripped between the housing and the anchor.

20. The cannula assembly of claim 19, which further comprises a cutting member to remove a portion of the cannula.

21. The cannula assembly of claim 19, wherein the housing is mounted for axial rotation with respect to the shortenable cannula.

22. The cannula assembly of claim 21, wherein the cutting member is configured to detach portions of the cannula in response to relative axial rotation of the housing with respect to the cannula.

23. The cannula assembly of claim 22, wherein the housing defines a cavity for storing the portions of cannula removed by the cutting member.

24. The cannula assembly of claim 19, wherein at least a portion of the cannula has a helical scoring formed thereon to facilitate removal of portions of the cannula.

25. The cannula assembly of claim 19, which further comprises a seal between the housing and the cannula.

26. The cannula assembly of claim 19, which further comprises a gripping member disposed on the cannula and configured to releasably secure a tool means inserted through the cannula.

* * * * *